United States Patent [19]

Wu

[11] Patent Number: 4,557,259

[45] Date of Patent: Dec. 10, 1985

[54] SURGICAL METHOD AND APPARATUS FOR INSERTING WIRE INTO THE SPINE

[75] Inventor: Kent K. Wu, Royal Oak, Mich.

[73] Assignee: Henry Ford Hospital, Detroit, Mich.

[21] Appl. No.: 521,683

[22] Filed: Aug. 10, 1983

[51] Int. Cl.[4] .............................................. A61F 5/04
[52] U.S. Cl. .................. 128/92 E; 128/341; 128/343; 128/92 R; 128/303 R
[58] Field of Search ............... 128/69, 92 R, 92 E, 128/303 R, 309, 341, 343, 340

[56] References Cited

U.S. PATENT DOCUMENTS

| | | | |
|---|---|---|---|
| 672,377 | 4/1901 | Kearns | 128/343 |
| 829,409 | 8/1906 | Manning | 128/341 |
| 919,138 | 4/1909 | Drake et al. | 128/340 |
| 1,641,077 | 8/1927 | Fouquet | 128/92 E |
| 2,897,820 | 8/1959 | Tauber | 128/340 |
| 4,244,370 | 1/1981 | Furlow et al. | 128/303 R |
| 4,312,337 | 1/1982 | Donohue | 128/92 E |
| 4,347,845 | 9/1982 | Mayfield | 128/92 E |
| 4,448,191 | 5/1984 | Rodnyansky et al. | 128/69 |
| 4,461,281 | 7/1984 | Carson | 128/343 |
| 4,467,800 | 8/1984 | Zytkovicz | 128/303 R |

FOREIGN PATENT DOCUMENTS 850062  7/1981  U.S.S.R. ................... 128/69

Primary Examiner—Gene Mancene
Assistant Examiner—C. W. Shedd
Attorney, Agent, or Firm—Barnes, Kisselle, Raisch, Choate, Whittemore & Hulbert

[57] ABSTRACT

A surgical method and apparatus for placing wire is utilized in close proximity to the spinal cord wherein a first tool having a thin tip is inserted between the ligament closest to the spinal cord and the associated vertebra, the first tool is manipulated to form a small passage, a second tool having a thicker tip is inserted into said passage and manipulated said tool to enlarge the passage further, and a third tool having a tubular tip is inserted into said passage and held in position so that a wire can be threaded through the opening of the tubular tip, after which the third tool with the tubular tip is removed leaving the wire in the passage that has been created between the ligament and the vertebra.

4 Claims, 14 Drawing Figures

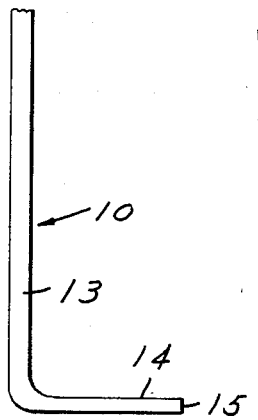
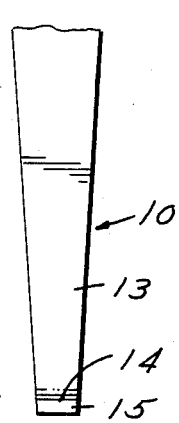
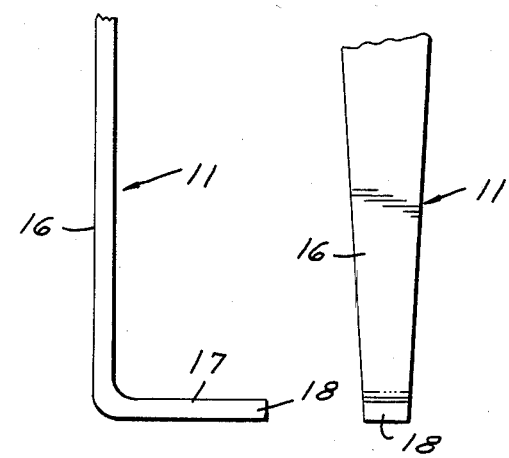
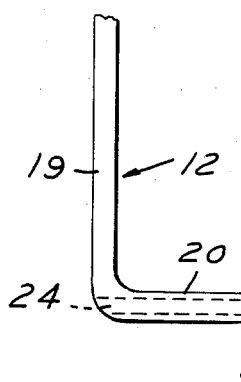
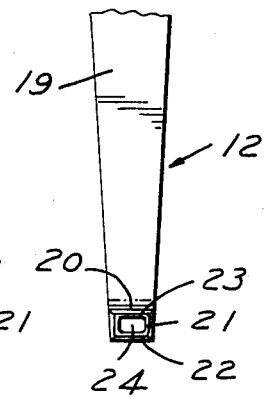
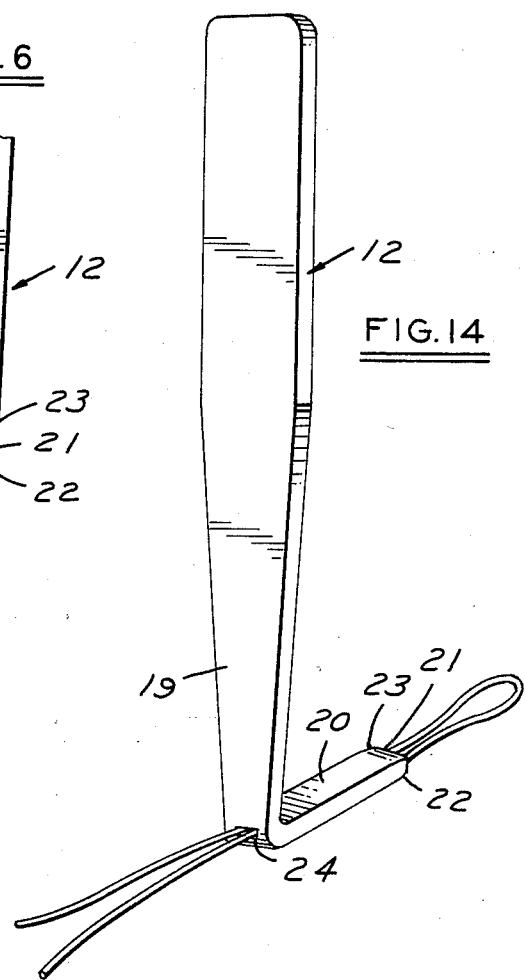

SURGICAL METHOD AND APPARATUS FOR INSERTING WIRE INTO THE SPINE

This invention relates to surgical procedures wherein wire is utilized in the spine in close proximity to the spinal cord.

BACKGROUND AND SUMMARY OF THE INVENTION

In surgical methods involving the spine, it is common to remove portions of the spine and to then apply bone grafts and the like that are held in position by wire. The insertion of the wire in close proximity to the spinal cord offers extreme danger especially since the area is difficult to observe.

Accordingly, among the objectives of the present invention are to provide a method and series of tools which can be utilized for insertion of the wire in close proximity to the spinal cord while minimizing the risk of possible injury to the spinal cord, minimizing intraoperative bleeding; and greatly reduce the operative time and thus minimize both intraoperative and postoperative complications such as bleeding and infection.

In accordance with the invention, a plurality of tools are used to progressively form a passage between the ligament closest to the spinal cord and the associated vertebra through which a wire to be utilized in spinal fusion is inserted so that the ligament serves as a protective wall between the wire and the spinal cord minimizing the risk of possible injury to the spinal cord.

DESCRIPTION OF THE DRAWINGS

FIG. 1 is a fragmentary side elevational view of a first tool utilized in accordance with the invention.

FIG. 2 is an end view of the first tool.

FIG. 3 is a fragmentary side elevational view of a second tool utilized in accordance with the invention.

FIG. 4 is an end view of the second tool.

FIG. 5 is a fragmentary side elevational view of a third tool utilized in the invention.

FIG. 6 is an end view of the third tool.

FIG. 14 is a perspective view of the third tool as used in a different manner.

DESCRIPTION

Figure 7:
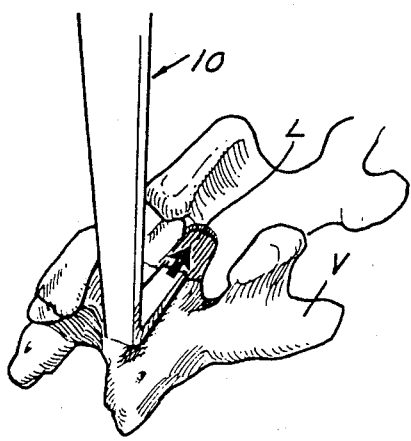
FIGS. 7-13 are fragmentary perspective views showing the use of the tools and performing the method.

Referring to FIGS. 1-6, the invention comprises the use of preferably three tools 10, 11 and 12. The first tool 10 includes an elongated handle 13 and a flattened tip 14 at the lower end at a right angle to the handle 13, the tip having a greater width than thickness and the free end being flattened as at 15. The second tool 11 similarly has a handle 16 and a flattened tip 17 at a right angle to the handle with a flattened end 18. The tip 17 is also wider than it is thick but the thickness of the tip 17 of the second tool 11 is greater than the thickness of the tip 14 of the first tool 10 for purposes presently to be described. The third tool 12 similarly includes a handle 19 and a top 20 at a right angle to the handle 20 and having a greater width than thickness and a flattened tip or end 21 with slightly inwardly tapered portions 22, 23. The tip 20 further includes a passage 24 open at both ends.

Figure 8:
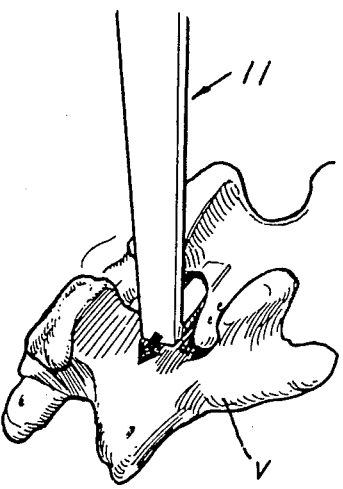
Figure 9:
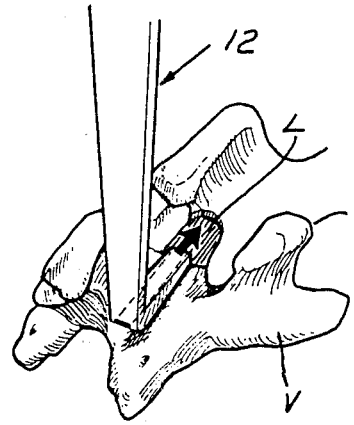
Figure 10:
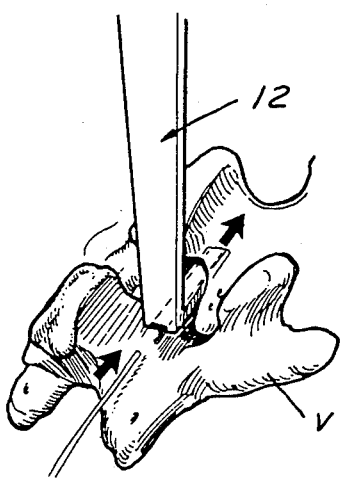
Figure 11:
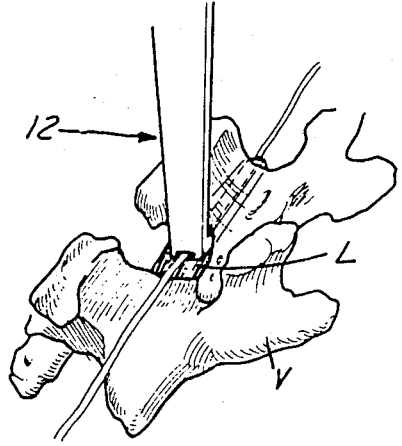
Figure 12:
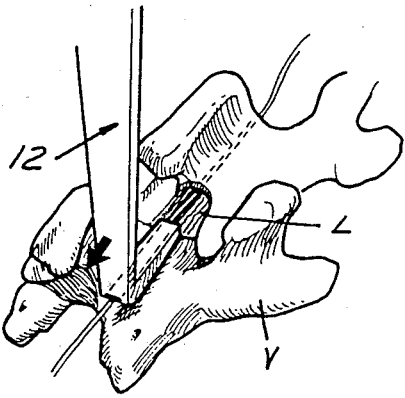
Figure 13:
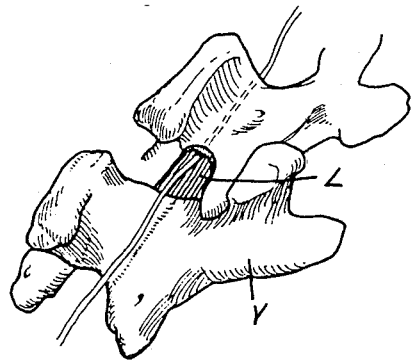

Referring to FIGS. 7-13, the method involves a series of steps wherein the first tool 10 is inserted between the ligament L and the vertebra V and manipulated to form a passage, the first tool 10 is removed and the second tool 11 is manipulated to insert the tip into the passage and manipulated to further enlarge the passage and is then removed. The third tool 12 is then inserted into the previously formed passage and held in position while the wire W is passed through the passage 24 of the tool after which the wire is held in position and the tool retracted leaving the wire in position.

It can thus be seen that the method and apparatus provides for positioning of the wire without exposing the spinal cord to the wire thereby minimizing the risk of possible injury to the spinal cord.

Although the method has been described in connection with the use of three tools, it can be appreciated that depending upon the size of the patient and the circumstances, the use of only the first tool 10 or the second tool 11 followed by the third tool 12 can be sufficient to provide the passage for the insertion of the third tool.

Although the threading of the wire is shown as a single wire, the side opening 24 permits a doubled wire to be guided as shown in FIG. 14.

It will be recognized that the invention has been described as applied to forming a passage between the ligament known as ligamentum flavrum and the portion of the vertebra known as the lamina.

In accordance with the invention, the method and tools minimize the risk of possible injury to the spinal cord, minimize intraoperative bleeding since tunneling is through a small area under the roof of the posterior neural arch and greatly reduce the operative time and thus minimize both intraoperative and postoperative complications such as bleeding and infection.

Although the invention has been described in connection with spinal fusion where the laminae provide the fusional surface where spinal fusion is utilized in fractures, dislocations, spinal fusions and infections, it is also useful in other applications. These include reduction of dislocations of the spine wherein forces are applied through the laminae to achieve reduction and the fixation of various internal fixation devices such as Luque rods and Harrington's spinal instrumentation wherein laminae are utilized for fixation of such devices.

I claim:

1. In the surgical method wherein wire is utilized in close proximity to the spinal cord, the steps of
    inserting a first L-shaped tool having a thin straight tip between the ligament closest to the spinal cord and the associated vertebra,
    manipulating the tool to form a small straight passage,
    inserting a second L-shaped tool having a straight tubular tip defining a straight passage extending entirely through the tip into said passage made by the first tool, holding said tool with the tubular tip in position and threading a wire through the opening of the tubular tip,
    holding the wire in said passage, and
    removing the tool with the tubular tip while holding the wire in the passage that has been created between the ligament and the vertebra.

2. The method set forth in claim 1 including the step of inserting a third L-shaped tool having a straight tip thicker than the tip of the first tool into said passage and manipulating said tool to enlarge the straight passage made by the first tool further, prior to insertion of the second tool with the tubular tip.

3. Surgical apparatus comprising
    a first L-shaped rigid tool having an elongated handle and a straight flattened tip at a generally right angle to the handle for insertion of the tip between a ligament and a vertebra to form a passage, and a rigid second L-shaped tool having an elongated handle and a straight tubular tip and having an open ended opening for insertion in said passage made by the first tool; said opening being straight and extending throughout the length of the tip such that the opening forms a guide for inserting wire in the passage, 4. The apparatus set forth in claim 3 including a third L-shaped rigid tool having an elongated handle and a straight tip at a generally right angle to said handle wherein said tip has a greater thickness than the first tool for subsequent insertion in the passage that has been formed by the first tool to enlarge the passage prior to insertion of the second tool with the tubular tip.

* * * * *